United States Patent
Iwamoto et al.

(10) Patent No.: US 9,199,094 B2
(45) Date of Patent: Dec. 1, 2015

(54) CHARGED PARTICLE BEAM IRRADIATION SYSTEM AND OPERATING METHOD OF CHARGED PARTICLE BEAM IRRADIATION SYSTEM

(75) Inventors: Tomohisa Iwamoto, Tokyo (JP); Kunio Moriyama, Tokyo (JP); Hideaki Nishiuchi, Tokyo (JP); Hideaki Nihongi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/238,068

(22) PCT Filed: Aug. 31, 2011

(86) PCT No.: PCT/JP2011/069835
§ 371 (c)(1),
(2), (4) Date: Mar. 24, 2014

(87) PCT Pub. No.: WO2013/030996
PCT Pub. Date: Mar. 7, 2013

(65) Prior Publication Data
US 2014/0203186 A1 Jul. 24, 2014

(51) Int. Cl.
*A61N 5/00* (2006.01)
*A61N 5/10* (2006.01)
(Continued)

(52) U.S. Cl.
CPC .......... *A61N 5/1067* (2013.01); *A61N 5/1075* (2013.01); *H05H 7/12* (2013.01); *H05H 13/04* (2013.01); *A61N 5/1079* (2013.01);
(Continued)

(58) Field of Classification Search
CPC ....................................... H05H 7/10
USPC ............................................. 250/492.1, 397
See application file for complete search history.

(56) References Cited

U.S. PATENT DOCUMENTS 5,260,581 A 11/1993 Lesyna et al.
5,363,008 A 11/1994 Hiramoto et al.
(Continued)

FOREIGN PATENT DOCUMENTS

JP 01-305391 A 12/1989
JP 04-118553 A 4/1992
(Continued)

OTHER PUBLICATIONS

Japanese Office Action received in corresponding Japanese Application No. 2013-530972 dated Jul. 8, 2014.
(Continued)

*Primary Examiner* — Phillip A Johnston
(74) *Attorney, Agent, or Firm* — Mattingly & Malur, PC (57) ABSTRACT

A charged particle beam irradiation system in which the energy, Bragg peak, and irradiation depth of a charged particle beam, with which a patient is to be irradiated, can be checked in real time just before actual irradiation. Just before the actual irradiation, by providing a high-speed steering magnet with 100% current, a checking beam is intentionally hit into a beam damper. By using a dosimeter and a dose measuring device in front thereof, extraction beam intensity is measured. By using a multi-layer beam monitor, a dose distribution thereof is measured. Accordingly, just before the actual irradiation, the energy, Bragg peak, and irradiation depth of the charged particle beam, with which the patient is to be irradiated, can be checked accurately and in real time. When the beam has a desired dose distribution as a result of checking, continuously, extraction control is performed.

6 Claims, 6 Drawing Sheets

(51) Int. Cl.
*H05H 7/12* (2006.01)
*H05H 13/04* (2006.01)
*H05H 7/00* (2006.01)
*H05H 7/04* (2006.01)

(52) U.S. Cl.
CPC .. *A61N2005/1087* (2013.01); *H05H 2007/008* (2013.01); *H05H 2007/046* (2013.01)

(56) References Cited

U.S. PATENT DOCUMENTS

| | | | |
|---|---|---|---|
| 6,683,318 | B1 | 1/2004 | Haberer et al. |
| 7,875,868 | B2 * | 1/2011 | Moriyama et al. ......... 250/492.3 |
| 2011/0231147 | A1 * | 9/2011 | Takayanagi et al. .......... 702/150 |

FOREIGN PATENT DOCUMENTS

| | | | |
|---|---|---|---|
| JP | 05-147793 A | 6/1993 |
| JP | 06-107362 A | 4/1994 |
| JP | 11-260356 A | 9/1999 |
| JP | 2001-004535 A | 1/2001 |
| JP | 2001-332248 A | 11/2001 |
| JP | 2002-525135 A | 8/2002 |
| JP | 2003-053759 A | 2/2003 |
| JP | 2005-127882 A | 5/2005 |
| JP | 3937561 B2 | 4/2007 |
| JP | 2008-226740 A | 9/2008 |
| JP | 2010-175309 A | 8/2010 |
| WO | 2006/080045 A1 | 8/2006 |

OTHER PUBLICATIONS

Chu et al., "Instrumentation for treatment of cancer using proton and light-ion beams", Review of Scientific Instruments, Aug. 1993, pp. 2074-2093, vol. 64, No. 8.

Proceedings of the Symposium on Accelerator and Related Technology for Application, Jun. 2005, pp. 35-36, vol. 7.

* cited by examiner

CHARGED PARTICLE BEAM IRRADIATION SYSTEM AND OPERATING METHOD OF CHARGED PARTICLE BEAM IRRADIATION SYSTEM

TECHNICAL FIELD

The present invention relates to a charged particle beam irradiation system, and more particularly, to charged particle beam irradiation system suitable for being applied to a particle beam therapy apparatus for treating an affected part by irradiating the affected part with charged particle beam such as a proton and a carbon ion.

BACKGROUND ART

There has been known a treatment method in which an affected part of a patient suffering from cancer and the like is irradiated with a charged particle beam (ion beam) such as a proton and carbon ion. A charged particle beam irradiation system (particle beam extraction system or charged particle beam extraction device) used in this treatment is provided with a charged particle beam generator, and the ion beam accelerated in the charged particle beam generator reaches an irradiation device installed in a rotating gantry by passing through a first beam transport line and a second beam transport line provided in the rotating gantry. The ion beam is extracted from the irradiation device, and the affected part of the patient is then irradiated with the ion beam. As the charged particle beam generator, for example, there is known a synchrotron (circular accelerator) provided with a unit for causing a charged particle beam to revolve along an orbit, a unit for bringing a betatron oscillation of the charged particle beam into a resonance state outside a stability limit of resonance, and an extraction deflector for taking out the charged particle beam from the orbit (see, for example, PTL 1).

The irradiation device shapes the ion beam lead from the above-described ion beam generator according to the depth of the affected part from a body surface of the patient and a shape of the affected part, and then irradiates the affected part of the patient on a treatment couch with the ion beam. In general, an irradiation device irradiates an affected part with an ion beam by using any of the beam irradiation methods including the double scattering irradiation method (NPTL 1, page 2081, FIG. 35), the Wobbler method (NPTL 1, page, 2084, FIG. 41), and the beam scanning irradiation method (PTL 2, and NPTL 1, pages 2092 and 2093).

Among the above-described beam irradiation methods, the beam scanning irradiation method is drawing attention as it has less influence on normal cells and requires no device incorporating a nozzle. The beam scanning irradiation method is characterized by irradiation of a beam according to a shape of the affected part by combining scanning in a direction perpendicular to a beam travelling direction by controlling a current amount for exciting a scanning magnet, and scanning in a depth direction of the affected part by changing energy.

In the beam scanning irradiation method, each element constituting an irradiation region is referred to as a spot, and an affected part divided into multiple regions in the depth direction is referred to as a layer. A current value the scanning magnet is set, and a set dose of irradiation is performed when reaching a target spot. Once the irradiated dose reaches a set value, an irradiation position is moved to the next spot. During a move from a spot to the next, extraction/of the beam is stopped. Once the move of the irradiation position is completed, the beam is extracted again. This is repeated until the irradiation is completed within one layer. Once the irradiation within one layer is completed, a similar irradiation is repeated by changing to energy for the next layer. This is repeated until the irradiation is completed in all layers. This is an outline of the beam scanning irradiation method.

When a charged particle beam is injected into a material (a body of a patient), it has a physical property to release most of the kinetic energy thereof just before stopping, and to form a dose distribution having a maximum called the Bragg peak. By adjusting the energy of the charged particle beam and by substantially aligning the Bragg peak with a position of the affected part in the depth direction, it is possible to give an intensive dose to the affected part.

A multi-layer beam monitor is an example of a unit for measuring the dose distribution. The multi-layer beam monitor has a dose measuring unit constituted by layering a plurality of ion chambers. The multi-layer beam monitor can measure the dose distribution inside the multi-layer beam monitor accurately and promptly in one irradiation (PTL 3). In general, the multi-layer beam monitor is disposed in a position downstream of the irradiation device where the patient is originally to be disposed. Prior to actual irradiation of the patient, by measuring the dose distribution by irradiating the multi-layer beam monitor, it is possible to check whether or not the predetermined energy, Bragg peak, and irradiation depth are realized.

Now, as a technology for efficiently irradiating an affected part with a beam, multi-energy extraction is drawing attention (PTL 4). In general, one cycle of a charged particle beam irradiation system includes injection-acceleration-extraction-deceleration, and a beam is extracted in multiple cycles while changing the energy. Meanwhile, in the multi-energy extraction, irradiation is performed in multiple different energies in one cycle such as injection-acceleration-extraction-acceleration-extraction-(repeated)-extraction-deceleration, or injection-acceleration-extraction-acceleration-extraction-(repeated)-extraction-deceleration-extraction-deceleration-extraction-(repeated)-extraction-decelerate. By using the multi-energy extraction, irradiation of the whole affected part can be completed in one cycle of operation of the synchrotron.

On the other hand, in the charged particle irradiation system, among the charged particle beams extracted from the charged particle beam generator, there may be an unnecessary charged particle beam not transported to the irradiation device. In order to process such unnecessary beam, it has been considered to provide a beam damper device in a first beam transport line (PTL 5).

CITATION LIST

Patent Literatures

PTL 1: U.S. Pat. No. 5,363,008
PTL 2: JP Patent No. 259629
PTL 3: JP 2010-175309 A
PTL 4: JP 2008-226740 A
PTL 5: U.S. Pat. No. 5,260,581

Non-Patent Literatures

NPTL 1: REVIEW OF SCIENTIFIC INSTRUMENTS, Volume 64, Number 8 (August, 1993), pages 2074-2093.
NPTL 2: Proceedings of the Symposium on Accelerator and Related Technology for Application, Volume 7 (June, 2005), pages 35-36.

SUMMARY OF INVENTION

Technical Problem

A multi-layer beam monitor in a prior art (PTL 3) is disposed in a position downstream of the irradiation device where a patient is originally to be disposed. Prior to actual irradiation of the patient, by measuring a dose distribution by irradiating the multi-layer beam monitor, the predetermined energy, the Bragg peak, and the irradiation depth can be checked.

Meanwhile, there is a demand from an operator who actually performs the irradiation for checking the energy, the Bragg peak, and the irradiation depth of a charged particle beam, with which the patient is to be irradiated, in real time as a final check just before the actual irradiation.

In particular, in a multi-energy extraction (PTL 4), it is important to check the energy and the like in each step in real time since multiple energies are used in one cycle.

However, a charged particle beam measured by the multi-layer beam monitor in a prior art is still in an adjustment step, and is not a charged particle beam with which the patient is actually irradiated. In other words, using the prior art, it is not possible to measure the dose distribution in real time in a state where the patient is disposed.

Furthermore, since the multi-layer beam monitor is on a side of the irradiation device, it is not possible to measure the dose distribution unless a beam extracted from a synchrotron is measured by the multi-layer beam monitor through a transport line, a gantry, and an irradiation device.

Therefore, it is not possible to measure the dose distribution in a system construction stage; it is necessary to wait until completion of the irradiation device. Furthermore, even after the completion of the system, when a failure of an extraction beam, occurs, it is not easy to know if the failure is due to a failure in an extraction beam of the synchrotron or due to a malfunction of any other device after the synchrotron, whereby it takes time in investigation.

Furthermore, in a system in which a beam damper device is installed in the first beam transport line (PTL 5), in a case where an unnecessary beam is generated among the charged particle beams extracted from the charged particle beam generator, it is possible to send the beam to the beam dump device to be processed therein. However, in a system according to the prior art, the beam dump device is used only for discarding the unnecessary beam.

An objective of the present invention is to provide a charged particle beam irradiation system and a method of operating the charged particle beam irradiation system in which the energy, the Bragg peak, and the irradiation depth of a charged particle beam, with which a patient is to be irradiated, can be checked in real time just before the actual irradiation.

Solution to Problem (1) In order to achieve the above-described objective, an operating method of a charged particle beam irradiation system according to the present invention having synchrotron including, in one operating cycle thereof, steps of injection-capturing, accelerating, extraction controlling, and decelerating, the operating method includes: extracting a part of a charged particle beam accumulated in the synchrotron as a checking beam before an extraction start in the extraction controlling; and at the same time, diverging the checking beam extracted from the synchrotron by controlling excitation of a steering electromagnet provided in a transport line downstream of the synchrotron and hitting the checking beam into a beam dump; and measuring a dose distribution of the charged particle beam to be hit into the beam dump by a multi-layer beam monitor provided in a divergent pathway; and saving and managing the measured dose distribution of the charged particle beam.

Accordingly, in a general synchrotron operating cycle, the energy, the Bragg peak, and the irradiation depth of the charged particle beam with which the patient is to be irradiated can be checked in real time just before an actual irradiation.

(2) In order to achieve the above-described objective, an operating method of a charged particle beam irradiation system according to the present invention having synchrotron configured to perform extraction control in each step by accelerating and decelerating a charged particle into different energies multiple times in one operating cycle thereof, the operating method includes: extracting a part of the charged particle beam accumulated in the synchrotron as a checking beam before an extraction start in the extraction control in each step; and at the same time, diverging the checking beam extracted from the synchrotron by controlling excitation of a steering electromagnet provided in a transport line downstream of the synchrotron and hitting the checking beam into a beam dump; measuring a dose distribution of the charged particle beam to be hit into the beam dump by a multi-layer beam monitor provided in a divergent pathway, and saving and managing the measured dose distribution of the charged particle beam.

Accordingly, in the multi-energy extraction, the energy, the Bragg peak, and the irradiation depth of the charged particle beam with which a patient is to be irradiated can be checked in real time just before an actual irradiation in each step.

(3) In order to achieve the above-described objective, a charged particle beam irradiation system according to the present invention includes: a charged particle beam generator configured to accelerate and extract a charged particle beam; a first beam transport line connected to the charged particle beam generator and configured to transport the charged particle beam extracted from the charged particle beam generator; and at least one irradiation device configured to perform irradiation with the charged particle beam. The charged particle beam irradiation system further includes: a high speed steering system having a steering electromagnet provided in the middle of the first beam transport line, and a beam dump provided in a beam pathway diverged from the steering electromagnet, and configured to hit the charged particle beam, not transported to the irradiation device among the charged particle beams extracted from the charged particle beam generator, into the beam dump by controlling excitation of the steering electromagnet; a multi-layer beam monitor provided in the high speed steering system and configured to measure a dose distribution of the charged particle beam to be hit into the beam dump; and irradiation management devices configured to save and manage the dose distribution of the charged, particle beam measured by the multi-layer beam monitor.

Accordingly, the checking beam extracted from the charged particle beam generator is not transported to the irradiation device and can be measured by the multi-layer beam monitor provided in the divergent pathway.

(4) In the above-described (3), preferably, there is further provided a dose monitoring device provided upstream of the multi-layer beam monitor inside the high speed steering system and configured to measure a dose of the charged particle beam. The irradiation management device saves and manages a dose value of the charged particle beam measured by the dose monitoring device.

Accordingly, a problem arising from hitting the checking beam into the beam dump can be resolved.

(5) In the above-described (3) and (4), preferably, there is further provided: a first controller configured to control an extraction start and an extraction stop of the charged particle beam from the synchrotron; a second controller configured to extract a part of the charged particle beam accumulated in the synchrotron as a checking beam before the extraction start in an extraction control interval in an operating cycle of the synchrotron; and at the same time, by controlling the excitation of the steering electromagnet, to hit the checking beam extracted from the synchrotron into the beam dump.

Accordingly, it is possible to hit the checking beam into the beam dump.

Advantageous Effects of Invention

According to the present invention, by measuring dose distribution of a checking beam by using a multi-layer beam monitor provided in a high speed steering system, it is possible to check the energy, the Bragg peak, and the irradiation depth of a charged particle beam, with which a patient is to be irradiated, just before an actual irradiation in real time.

Furthermore, in a case where any unexpected deviation occurs to an extraction beam, it is possible to isolate whether or not the deviation factor is on the synchrotron side or on the side of the beam transport line, the irradiation device, or any other device, whereby a time-saving and an accuracy improvement can be expected in a measure against the deviation factor.

Furthermore, in a system construction stage, an adjustment of the beam intensity of the extraction beam from the synchrotron can be performed even before completion of the irradiation device, whereby an early startup of the charged particle beam irradiation system becomes possible.

DESCRIPTION OF EMBODIMENTS

Embodiments of the present invention are described herein.

(Configuration)

Figure 1:
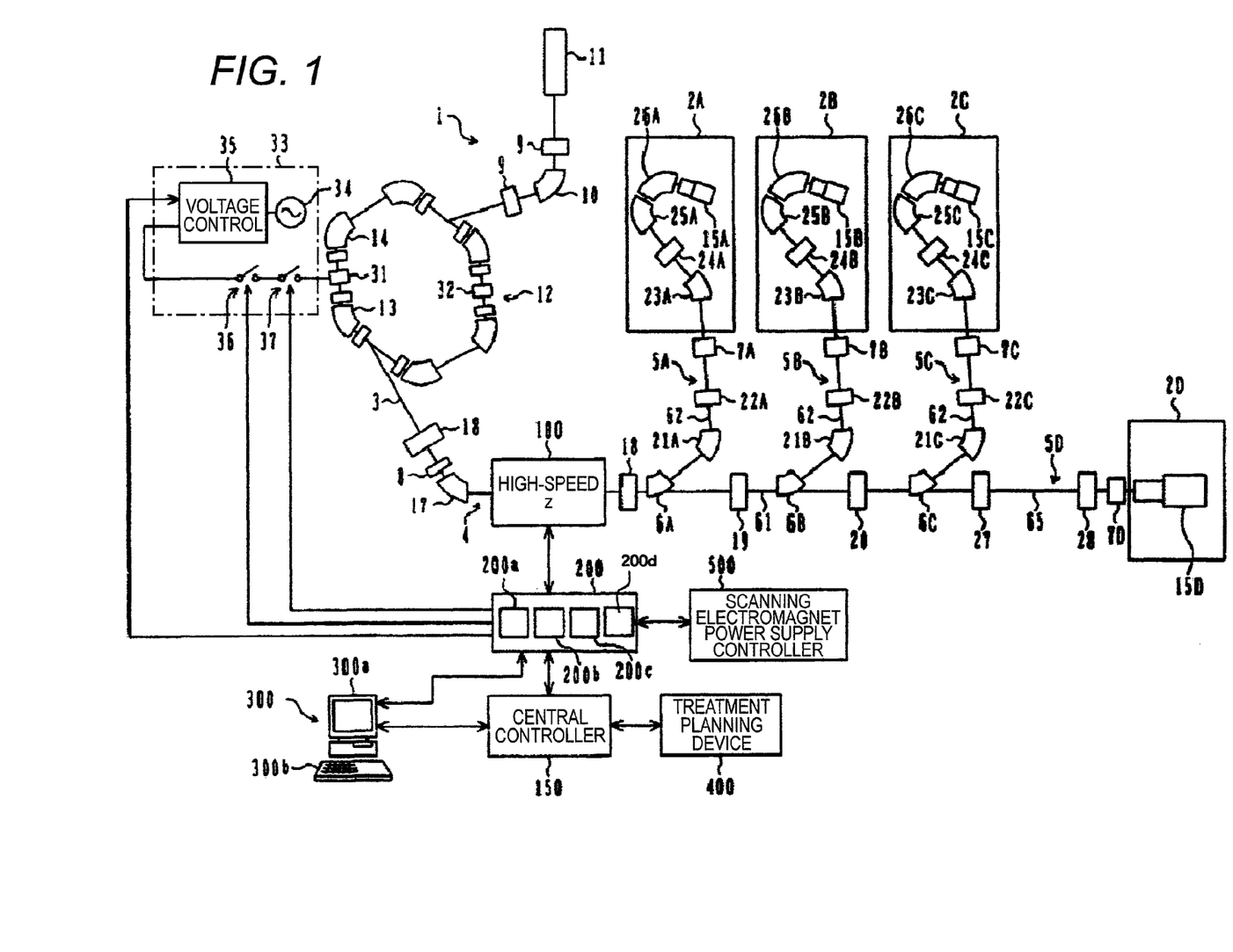
FIG. 1 is a schematic configuration diagram of a whole charged particle beam irradiation system.

As illustrated in FIG. 1, a charged particle beam irradiation system according to this embodiment is provided with: a charged particle beam generator 1; a first beam transport line 4 connected on a downstream side of the charged particle beam generator 1; second beam transport lines 5A, 5B, 5C, and 5D respectively provided so as to diverge from the first beam transport line 4; switching electromagnets (pathway switching devices) 6A, 6B, and 6C; and irradiation devices 15A, 15B, 15C, and 15D, which are irradiation field forming devices. The first beam transport line 4 is a common beam transport line for leading an ion beam to each of the second beam transport lines 5A, 5B, 5C, and 5D. The second beam transport lines 5A, 5B, 5C, and 5D are beam transport lines provided for the irradiation devices 15A, 15B, 15C, and 15D, respectively. The irradiation devices 15A, 15B, 15C, and 15D are disposed in treatment rooms 2A, 2B, 2C, and 2D. The charged particle beam irradiation system according to this embodiment is specifically a proton beam treatment system.

The charged particle beam generator 1 includes an ion source (not illustrated), a preliminary accelerator (for example, a linear accelerator) 11, and a synchrotron 12, which is a main accelerator. In the synchrotron 12, a radio frequencyradio frequency applying device 31 and a radio frequency acceleration cavity (accelerator) 32 are installed on an orbit of the charged particle beam. The radio frequency applying device 31 is provided with a pair of electrodes (not illustrated) for applying a radio frequency. The electrodes for applying the radio frequency are connected to a radio frequency supplying device 33 used for extraction. The radio frequency supplying device 33 is provided with a radio frequency oscillator (extraction radio frequency power supply) 34, an applying voltage controller (extraction beam intensity controller) 35, an interlocking switch (opening and closing device) 36, and an irradiation control switch (opening and closing switch) 37. The interlocking switch (opening and closing device) 36 is opened by an interlock signal, and is closed during normal times. The irradiation control switch (opening and closing switch) 37 is closed by a beam extraction start signal, and is opened by a beam extraction stop signal. The radio frequency applying device 31 receives a supply of the radio frequency voltage used for extraction from the radio frequency oscillator 34 through the applying voltage controller 35 and the switches 36 and 37. A radio frequency power supply (not illustrated) for applying radio frequency power to a radio frequency acceleration cavity 32 is separately provided.

An ion (for example, a positive ion (or a carbon ion)) generated in an ion source is accelerated in the preliminary accelerator 11. The charged particle beam extracted from the preliminary accelerator 11 is injected into the synchrotron 12. The charged particle beam is given energy based on an electromagnetic field generated inside the radio frequency acceleration cavity 32 by application of the radio frequency power from the radio frequency power supply; and is accelerated. The charged particle beam revolving inside the synchrotron 12 is, after being accelerated up to a set energy (for example, 100 to 200 MeV), by closing the opening and closing switch 37, a radio frequency from the radio frequency oscillator 34, which is an extraction radio frequency power supply, is applied to the revolving charged particle beam extraction by the radio frequency applying device 31. Therefore, the charged particle beam revolving within a stability limit transits to outside the stability limit and is extracted passing through a extraction deflector. At the time of extraction of the charged particle beam, a current lead by a quadrupole electromagnet 13 and a deflection electromagnet 14 provided in the synchrotron 12 is maintained to be a current set value, and the stability limit is also maintained to be substantially constant. By opening the opening and closing switch 37 and by stopping the application of the radio frequency power to the radio frequency applying device 31 for extraction, the extraction of the charged particle beam from the synchrotron 12 is stopped.

The charged particle beam extracted from the synchrotron 12 is transported to the downstream side by passing through the first beam transport line 4 and a high-speed steering system 100 (to be described later). The first beam transport line 4 is provided with a beam pathway 3; a quadrupole electromagnet 18, a shutter 8, a deflection electromagnet 17, another quadrupole electromagnet 18, switching electromagnet 6A, and a beam pathway 61 disposed in the beam pathway 3 from an upstream side thereof in a beam travelling direction; a quadrupole electromagnet 19, a switching electromagnet 6B, a quadrupole electromagnet 20, and a switching electromagnet 6C disposed in the beam pathway 3 from an upstream side thereof in a beam travelling direction beam. The charged particle beam extracted to the first beam transport line 4 is selectively led into any of the second beam transport lines 5A, 5B, 5C, and 5D depending on an existence or absence of a deflecting action by switching between excitation and non-excitation of the switching electromagnets 6A, 6B, and 6C.

The second beam transport line 5A includes: a beam pathway 62 connected to the beam pathway 3 of the first transport line 4 and communicates with an irradiation device 15A, which is disposed inside the treatment room 2A; and deflection electromagnet 21A, a quadrupole electromagnet 22A, a shutter 7A, a deflection electromagnet, 23A, a quadrupole electromagnet 24A, a deflection electromagnet 25A, and a deflection electromagnet 26A disposed in the beam pathway 62 from an upstream side thereof in a beam travelling direction.

The second beam transport line 5B and the second beam transport line 5C are configured similar to the second beam transport line 5A. Constituent elements of the second beam transport lines 5B and 5C equivalent to those of the second beam transport line 5A are denoted with the same reference numeral having a suffix B or C instead of a suffix A. The fourth beam transport line 5D is provided with a beam pathway 65 connected to the beam pathway 61 of the first transport line 4 and communicates with the irradiation device 15D disposed inside the treatment room 2D, and quadrupole electromagnets 27 and 28 and a shutter 7D disposed in the beam pathway 65 from an upstream side thereof in a beam travelling direction.

The charged particle beam lead into the second beam transport line 5A through the first beam transport line 4 is transported to the irradiation device 15A through the beam pathway 62 by excitation of a relevant electromagnet. Similarly in the second beam transport lines 5B, 5C, and 5D, the charged particle beam is transported to the irradiation devices 15B, 15C, and 15D, respectively, through each of the beam pathways 62, and the beam pathways 61 and 65, respectively.

The irradiation devices 15A to 15C are attached to respective rotating gantries (not illustrated) installed in the treatment rooms 2A to 2C. The irradiation device 15D is of a fixed type.

The irradiation devices 15A to 15D are provided with respective scanning magnets (not illustrated). By controlling a scanning magnet power supply (not illustrated) by a scanning magnet power supply controller 500, the excitation current is controlled, and a scanning with the charged particle beam is performed in a transverse direction. Furthermore, the irradiation devices 15A to 15D stops a move (scan) of the charged particle beam at each irradiation position to perform irradiation, and once an irradiated dose at the irradiation position reaches target value, moves to the next irradiation position. While moving the irradiation position to the next position, extraction of the charged particle beam from the synchrotron 12 is stopped. Once the move of the irradiation position is completed, the charged particle beam is extracted again from the synchrotron 12. Due to such control of the scanning magnet and ON/OFF control of the charged particle beam, the irradiation devices 15A to 15D have a dosimeter for detecting a dose (irradiated dose) of the charged particle beam and a position detection device for detecting the irradiation position, and output information on the irradiated dose and on the position to an acceleration-irradiation controller 200.

Furthermore, a charged particle beam irradiation system according to this embodiment is provided with high-speed steering system (high speed steering system) 100 provided in the first beam transport line 4. By controlling the high-speed steering system 100, it is possible to transport the charged particle beam extracted to the first transport line 4 to the succeeding second beam transport lines 5B, 5C, and 5D or to the high-speed steering system 100. By installing the high-speed steering system 100 right after the synchrotron 12 in the first beam transport line 4, the high-speed steering system, 100 is configured such that the charged particle beam reaching the high-speed steering system 100 does not pass through many devices in the beam transport line.

Figure 2:
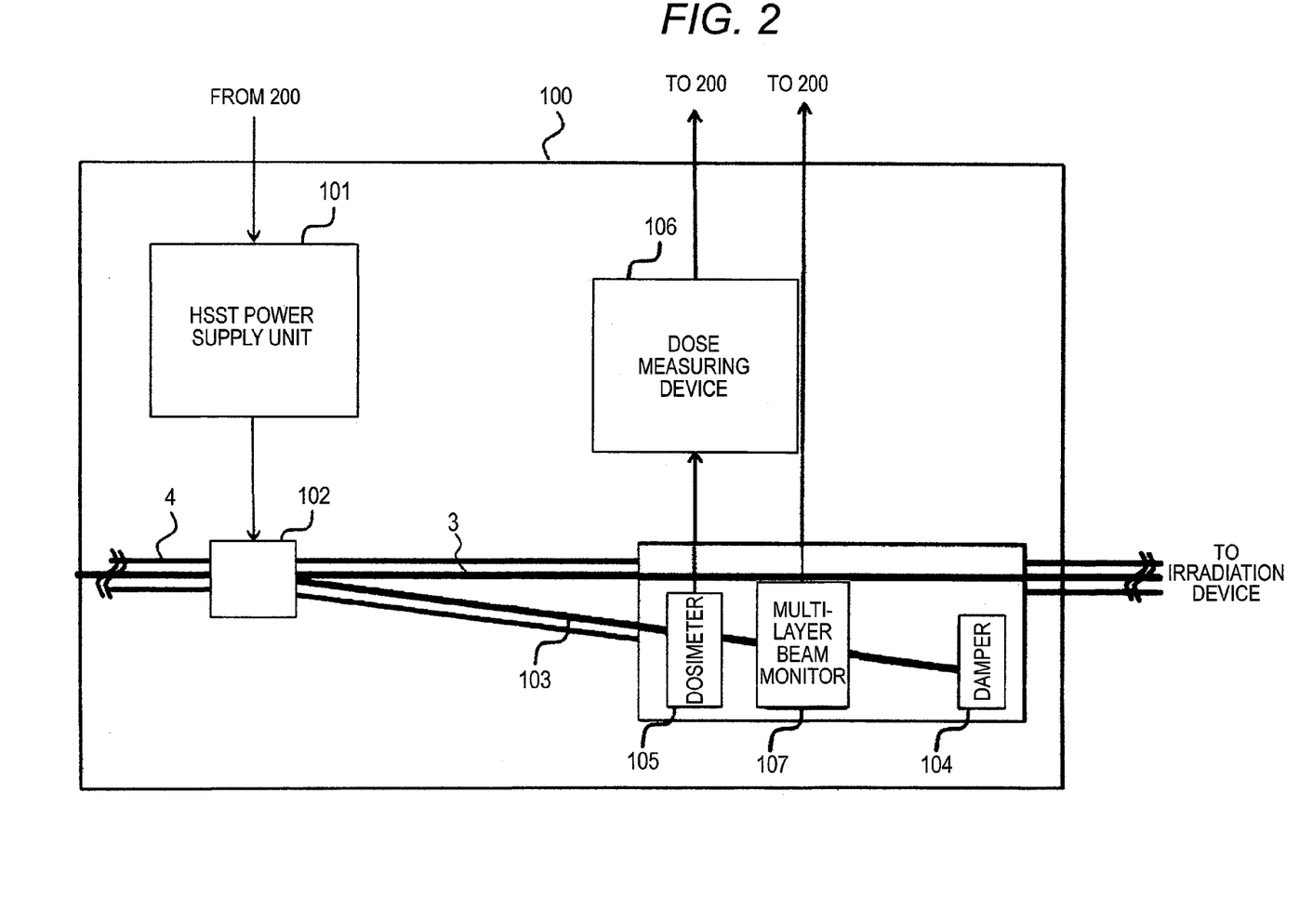
FIG. 2 is a detailed view of a configuration of high-speed steering system.

FIG. 2 is a view illustrating details of a configuration of the high-speed steering system 100.

The high-speed steering system 100 includes a high-speed steering (HSST) magnet 102 provided in the middle of the beam pathway 3 in the first beam transport line 4, and a beam dump 104 installed in a beam pathway 103 diverged from the high-speed steering magnet 102. The high-speed steering (HSST) magnet 102 is a steering electromagnet for bending a beam at a high speed, and for example, it can hit the beam right into the beam dump 104 at 100% current. Furthermore, at 0% current, it can directly let the beam to pass through it to a succeeding transport line without bending the beam.

Switching of the high-speed steering magnet 102 from the 100% current to the 0% current or from the 0% current to the 100% current can be performed by a high-speed steering power supply unit 101 at a high speed, for example, within 500µ seconds.

Furthermore, the high-speed steering system 100 according to the present, invention includes: a dosimeter 105 installed before the beam dump 104 in the beam pathway 103; a dose measuring device 106 for inputting measurement signal from the dosimeter 105; and a multi-layer beam monitor 107 installed between the dosimeter 105 and the beam dump 104. A dose of the beam hit into the beam dump 104 can be measured by processing the measurement signal from the dosimeter 105 in the dose measuring device 106. Furthermore, the dose measuring device 106 can measure the beam intensity by integrating the dose of the beam and by calculating an increment (amount of change in the dose value per unit time) thereof.

Figure 3:
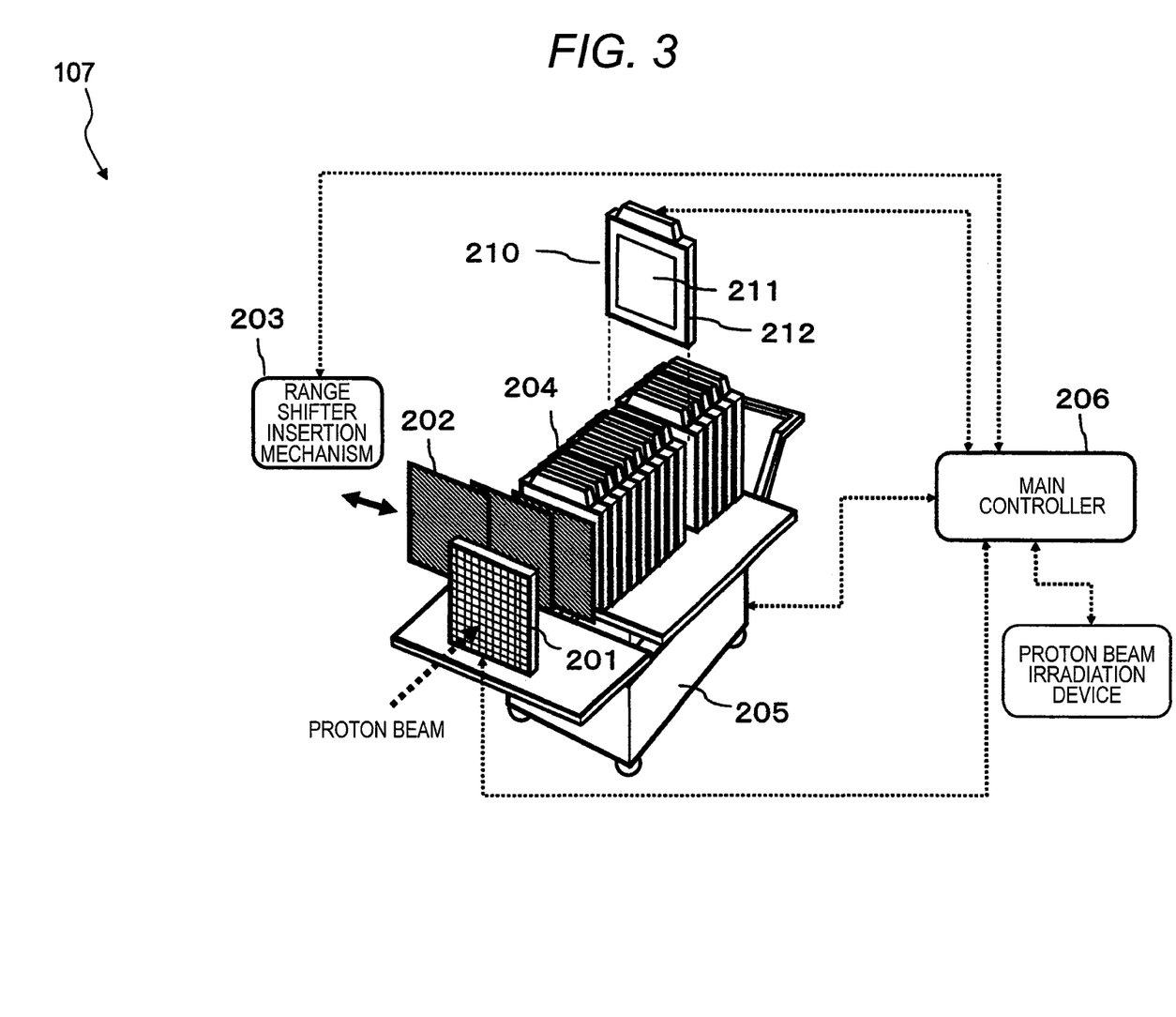
FIG. 3 is a configuration diagram of a multi-layer beam monitor.
Figure 4:
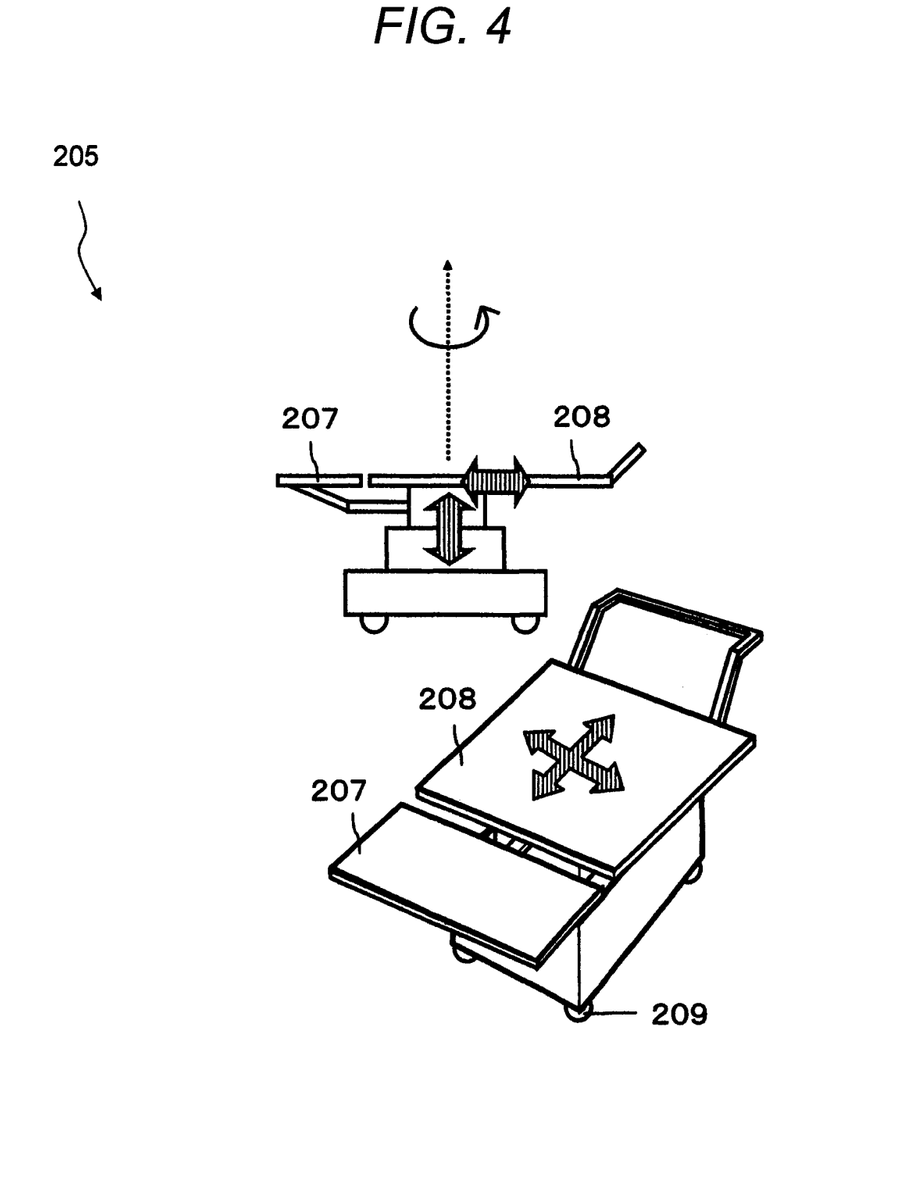
FIG. 4 is a movable device of the multi-layer beam monitor.

Then, a structure of the multi-layer beam monitor 107 is described herein by using FIGS. 3 and 4. The multi-layer beam monitor 107 includes a spot position monitor 201 (hereinafter, referred to as SPM), a range shifter 202, a range shifter insertion mechanism 203, a dose measuring unit 204, a movable device 205, and a main controller 206 (connected to a fourth control unit 200d described below).

The SPM 201 measures a centroid position in transverse direction of a beam that has entered the SPM 201. The SPM 201 is an ion chamber or a proportional counter tube in which a plurality of anode electrodes is disposed inside a gas container at an interval of several millimeters. It can accurately measure a centroid position of the beam and an expanse in a transverse direction thereof irradiated by using the scanning irradiation method and the like, by comparing with the dose measuring unit 204. Furthermore, the SPM 201 is detachable according to an adjustment item and a performance evaluation item of the multi-layer beam monitor 107.

The range shifter 202 changes a measurement position in a longitudinal direction according to the adjustment item and the performance evaluation item. Individuals varying in thickness are prepared, and depending on a combination thereof, a measurement range can be changed at a very close interval (for example, 0.1 mm) in the longitudinal direction. Note, however, that a type of a material and thickness of the range shifter 202 to be used is arbitrary according to the adjustment and performance evaluation items of the charged particle beam irradiation system. Furthermore, insertion of the range shifter 202 is realized by the range shifter insertion mechanism 203. In a movable device 205, the SPM 201, the range shifter 202, and the range shifter insertion mechanism 203 are disposed on a movable top plate A 207, and the dose measuring unit 204 is disposed on a movable top plate B 208.

The movable device 205 scans the movable top plate B 208 in a longitudinal direction 1 axis and a transverse direction 2 axis according the adjustment and performance evaluation items of the charged particle beam irradiation system. The movable top plate A 207, in link with the movable top plate B 208, moves in the transverse direction 2 axis. Furthermore, for an alignment of the multi-layer beam monitor 107, the movable device 205 can rotate the movable top plate A 207 and the movable top plate B 208 simultaneously around an axis in a direction perpendicular to the ground surface. Furthermore, device installation surfaces of the movable top plate A 207 and the movable top plate B 208 are adjusted so as to be parallel with the longitudinal direction. A wheel 209 is provided on a bottom surface of the movable device 205 such that the multi-layer beam monitor 107 can be moved to an arbitrary place for use. Note, however, that the multi-layer beam monitor 107 is fixed to a fixed position. The movable device 205 is used for making a fine-adjustment in aligning a beam center.

The dose measuring unit 204 includes tens of layers, of ion chambers 210 layered in a longitudinal direction. The ion chambers 210 are layered such that there is a little gap as possible between each of the ion chambers 210. The ion chambers 210 are detachable one by one, and it can be replaced immediately in a case where an ion chamber in a certain layer breaks down. Note, however, that the number of layers of the ion chambers 210 is arbitrary according to the adjustment and performance evaluation items of the charged particle beam irradiation system. The ion chambers 210 include a sensor 211 having sensitivity to a beam dose, and a signal processing device 212.

Then, going back to FIG. 1, a control system of the charged particle beam irradiation system according to this embodiment is described herein. The charged particle beam irradiation system, as a control system thereof, is provided with a central controller 150, an acceleration-irradiation controller 200, a terminal controller 300, and a scanning magnet power supply controller 500.

The acceleration-irradiation controller 200 has a plurality of controllers including a first control unit 200a, a second control unit 200b, a third control unit 200c, and a fourth control unit 200d.

In the first control unit 200a, based on information saved in a memory of the central controller 150, and irradiated dose information, position information, and the like from the irradiation devices 15A to 15D, generates a beam extraction start signal and a beam extraction stop signal. By outputting the beam extraction start signal and the beam extraction stop signal to the opening and closing switch 37, the extraction start and the extraction stop of the charged particle beam from the synchrotron 12 is controlled (first controller).

The third control unit 200c, based on the information stored in the memory of the central controller 150, and the irradiated dose information, the position information, and the like from the irradiation devices 15A to 15D, determines an excitation current of a scanning magnet for moving an irradiation position to the next position, and outputs this excitation current information to the scanning magnet power supply controller 500. The scanning magnet power supply controller 500, based on the excitation current information, controls the scanning magnet power supply (not illustrated), and controls the excitation current of the scanning magnet.

By controlling the extraction start and the extraction stop of the charged particle beam from the synchrotron 12 and the excitation current of the scanning magnet in this way, it is possible to scan an irradiation target with the charged particle beam in a transverse direction (a perpendicular direction (depth direction) in a travelling direction of the charged particle beam), and to control a dose distribution in the transverse direction to be a desired distribution. Details of this control are disclosed in JP Patent No. 2833602 and the like.

The second control unit 200b is connected to a power supply unit 101 of the high-speed steering system 100. By controlling the power supply unit 101, switching of a current amount of the high-speed steering magnet 102 is controlled.

The fourth control unit 200d is connected to the dose measuring device 106 and the multi-layer beam monitor 107 of the high-speed steering system 100. The fourth control unit 200d inputs and saves (records) the dose value, beam intensity, and the dose distribution, which are measured by the dosimeter 105, the dose measuring device 106, and the multi-layer beam monitor 107, in a memory. Furthermore, the saved dose value and the beam intensity are output to the terminal controller 300.

Another controller of the acceleration-irradiation controller 200, based on other information saved in the memory of the central controller 150, sets and controls a parameter of another device, such as the radio frequency acceleration cavity 32 constituting the charged particle beam generator 1, and of a controller therefor.

The terminal controller 300 has a monitor 300a and an input device 300b, such as a keyboard and a mouse, for performing a predetermined input through a user interface displayed on the monitor 300a. Furthermore, the terminal controller 300 can input and display a dose value and beam intensity, obtained from the dose measuring device 106 and saved in a memory of the second control unit 200b of the acceleration-irradiation controller 200, on the monitor 200a. Accordingly, the fourth control unit 200d of the acceleration-irradiation controller 200 and the terminal controller 300 constitute an irradiation management device for saving and managing the dose value, the beam intensity, and the dose distribution of the charged particle beam measured by the dosimeter 105, which is a dose monitoring device, the dose measuring device 106, and the multi-layer beam monitor 107.

(Operation)

First, operation according to this embodiment (first operation) is described herein.

Figure 5:
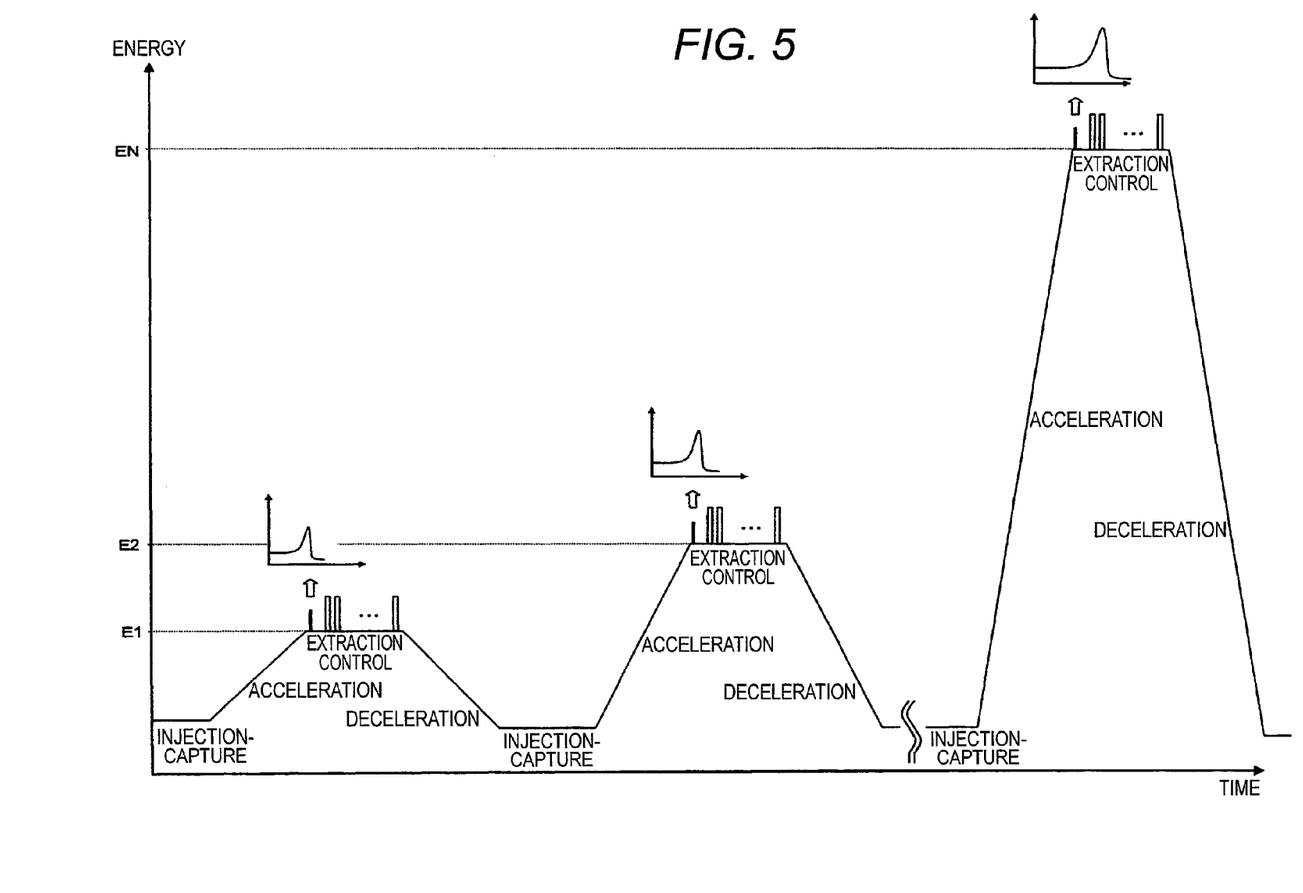
FIG. 5 is a view illustrating an operation in one cycle of a synchrotron in general.

FIG. 5 shows typical operating cycles of the synchrotron 12. Injection-capture of a charged particle beam, acceleration for increasing the charged particle beam to a set energy, extraction of the charged particle beam that has reached a target energy, and deceleration are included in one cycle. This operating cycle is repeated. Control of the injection-capture, the acceleration, the extraction, and the deceleration (one operating cycle of the synchrotron 12) is specified according to the energy of the charged particle beam to be accelerated. The charged particle beam revolving on an orbit of the synchrotron 12 is accelerated up to the target energy. Then, in an extraction control section, the radio frequency supplying device 33 is started up to operate the radio frequency applying device 31, and by applying a extraction radio frequency, the charged particle beam is extracted from the synchrotron 12 to the succeeding first beam transport line 4. Accordingly, the synchrotron 12 can supply the charged particle beam to the irradiation devices 15A to 15D in each of the treatment rooms 2A to 2D connected to the succeeding second beam transport lines 5A to 5D in the extraction control section.

With the beam scanning irradiation method, it is possible to irradiate a region (layer), which is the affected part divided into a depth direction, by scanning the region with a beam in a planar direction by using a scanning magnet and by on/off controlling the beam in the extraction control section. In order to irradiate the affected part entirely in the depth direction, irradiation of each layer is repeated by changing the energy.

Therefore, it is important that the energy, the Bragg peak, and the irradiation depth of the charged particle beam with which a patient is to be irradiated can be checked in real time just before an actual irradiation. A distinctive operation this embodiment is described herein.

By using the synchrotron 12, the first beam transport line 3, and the high-speed steering system 100, it is possible to measure the dose distribution of the extraction beam from the synchrotron 12.

That is, just before the actual irradiation, by providing the high-speed steering magnet 102 with 100% current, a checking beam is intentionally hit into the beam dump 104. By using the dosimeter 105 and the dose measuring device 106 in front thereof, intensity of the extraction beam is measured, and by using the multi-layer beam monitor 107, a dose distribution thereof is measured. Accordingly, just before the actual irradiation, the energy, the Bragg peak, and the irradiation depth of the charged particle beam with which the patient is to be irradiated can be checked accurately and in real time.

When the beam has a desired dose distribution as a result of checking, continuously, extraction control is performed. When the beam does not have a desired dose distribution, the beam is accelerated or decelerated, and again, checking beam is extracted, and the dose distribution is measured. When the beam still does not have the desired dose distribution even after an adjustment is made by accelerating or decelerating the beam, the operating cycle is ended, and extraction is performed again after a readjustment.

Next, an operation when the system according to this embodiment is applied to a multi-energy extraction (second operation) is described herein.

There has been much attention on the multi-energy extraction, in which a plurality layers can be irradiated with a plurality of energies in one cycle. In the multi-energy extraction, it is especially important to check the energy in each step in real time because it involves changes into a plurality of energies in one cycle.

Figure 6:
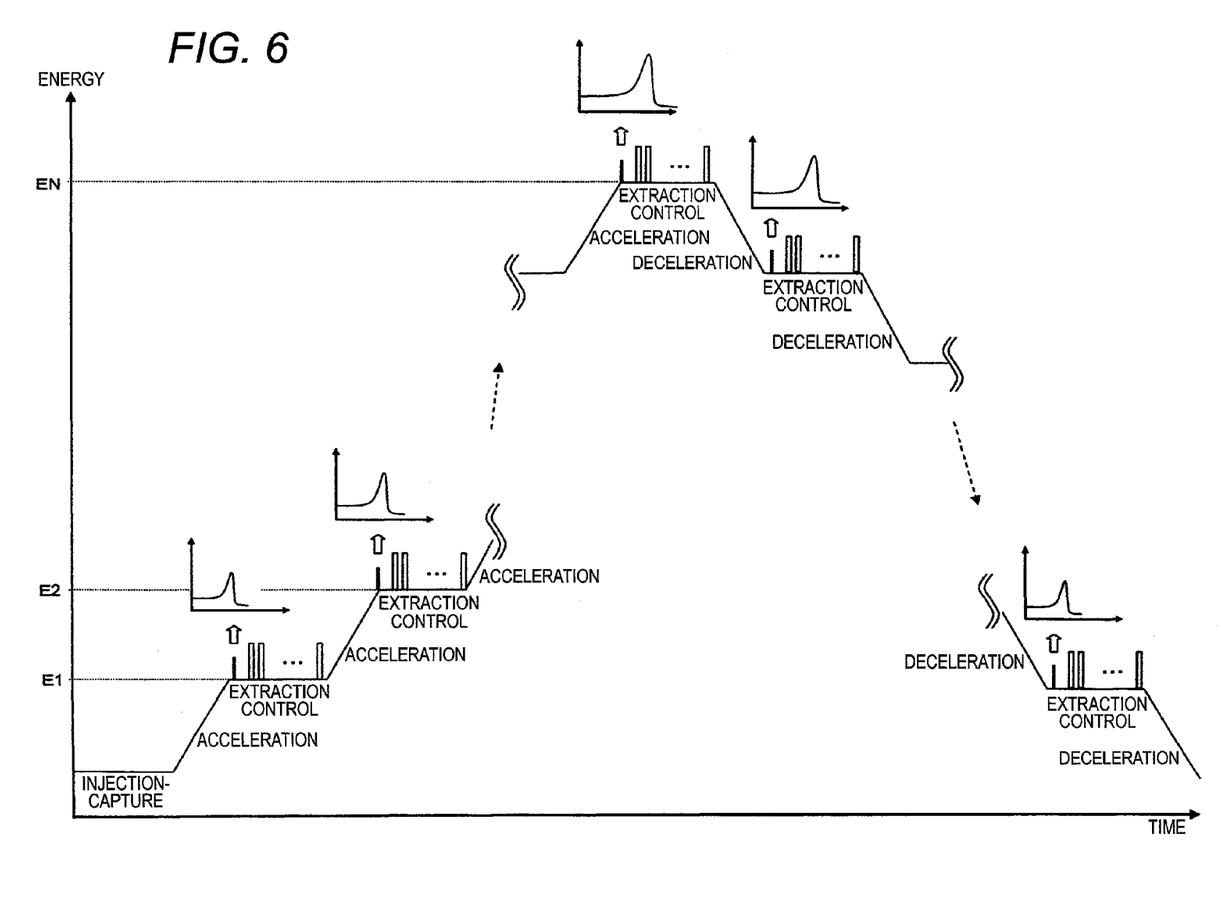
FIG. 6 is a view of an operating cycle of the synchrotron in a multi-energy extraction.

FIG. 6 is a view illustrating an operating cycle of the synchrotron 12 in the multi-energy extraction. The following is performed in one cycle: injection-capture of a charged particle beam; acceleration for increasing the charged particle beam up to a first step energy; extraction of the charged particle beam that has reached a target energy; acceleration for increasing up to the second step energy; extraction of the charged particle beam that has reached a target energy; --repeated-- acceleration for increasing up to the Nth step energy; extraction of the charged particle beam that has reached a target energy; deceleration to the N-1th step energy; extraction of the charged particle beam that has reached a target energy; --repeated-- and an end. It is possible to irradiate a layer corresponding to each step by scanning the layer with a beam in a planar direction by using a scanning magnet and by on/off controlling the beam in the extraction control section in each step.

Further in this embodiment, just before the actual irradiation in each step, by providing the high-speed steering magnet 102 with 100% current, a checking beam is intentionally hit into the beam dump 104. By using the dosimeter 105 and the dose measuring device 106 in front thereof, intensity of the extraction beam is measured, and by using the multi-layer beam monitor 107, a dose distribution thereof is measured. Accordingly, just before the actual irradiation, the energy, the Bragg peak, and the irradiation depth of the charged particle beam with which the patient is to be irradiated in each step can be checked accurately and in real time. When the beam has a desired dose distribution as a result of checking, continuously, extraction control is performed.

(Effect)

By using this embodiment configured as such, the following effects can be obtained.

A multi-layer beam monitor in a prior art is disposed in a position downstream of the irradiation device where the patient is originally to be disposed. Prior to actual irradiation of the patient, the dose distribution is measured by irradiating the multi-layer beam monitor. Therefore, it is not possible to measure the dose distribution in real time in a state where the patient is disposed.

According to this embodiment, it is possible to measure the dose distribution of the checking beam by the multi-layer beam monitor 107 inside the high-speed steering system 100 in real time.

Furthermore, in a case where any unexpected deviation occurs in the extraction beam, it is possible to isolate whether or not the deviation factor is on the synchrotron side or on the side of the first and second beam transport lines 4 and 5A to 5D, the irradiation, devices 15A to 15D, or any other device, whereby a time-saving and an accuracy improvement can be expected in a measure against the deviation factor.

Furthermore, in a system construction step, an adjustment of the beam intensity of the extraction beam from the synchrotron 12 can be performed even before completion of the irradiation device, whereby an early startup of the charged particle beam irradiation system becomes possible.

(Accompanying Configuration and Effect Thereof)

This embodiment is characterized by intentionally hitting a checking beam into a beam dump 104 and measuring a dose distribution thereof; whereby a problem as below newly arises.

In general, accompanied by extraction of a charged particle beam, an accumulated charge amount of the charged particle beam within the synchrotron 12 decreases, and beam intensity is lowered. To deal with this, the intensity of the extraction beam is made constant by measuring the beam intensity by using a dosimeter installed on the irradiation device side and, based on this measurement result, by calculating an applied voltage gain pattern for extraction radio frequency.

However, in this embodiment, since the checking beam is intentionally hit into the beam dump 104, the dosimeter installed on the irradiation device side cannot measure the beam intensity accurately.

In this embodiment, intensity of the checking beam is measured by the dosimeter 105 and the dose measuring device 106, and based on the measurement result, the fourth control unit 200d calculates the applied voltage gain pattern of the extraction radio frequency, and makes the intensity of the extraction beam constant. Accordingly, the intensity of the extraction beam can be made constant without being influenced by the checking beam extraction.

(Modification)

(1) In the operation 2, an exemplary operating cycle of the multi-energy extraction in FIG. 6 is illustrated; however, it may also be another operating cycle. For example, it is also possible to include the following in one cycle: injection-capture of a charged particle beam; acceleration for increasing the charged particle beam up to the first step energy; extraction of the charged particle beam that has reached a target energy; acceleration for increasing up to the second step energy; extraction of the charged particle beam that has reached a target energy; --repeated-- acceleration for increasing up to the Nth step energy; extraction of the charged particle beam that has reached a target energy; deceleration; and an end.

(2) A multi-layer beam monitor has been assumed as a unit for measuring a dose distribution in the description; however, it is also possible to use a water phantom.

(3) The beam scanning irradiation method has been assumed as the beam irradiation method in the description; however, it is also possible to use the scattering irradiation or the wobbler method.

REFERENCE SIGNS LIST 1 charged particle beam generator
2A-2D treatment room
4 first beam transport line
5A-5D second beam transport line
6A-6C switching electromagnet
7A-7D shutter
15A-15D irradiation device
31 radio frequency applying device
32 radio frequency acceleration cavity (accelerator)
33 radio frequency supplying device
34 radio frequency oscillator (extraction radio frequency power supply)
35 applying voltage controller (extraction beam intensity controller)
36 interlocking switch (opening and closing device)
37 irradiation control switch (opening and closing switch)
100 high-speed steering system (high speed steering system)
101 high-speed steering system power supply unit
102 high-speed steering magnet (steering electromagnet)
104 beam dumper
105 dosimeter (dose monitoring device)
106 dose measuring device (dose monitoring device)
107 multi-layer beam monitor
150 central controller
200 acceleration-irradiation controller
200a first control unit (first controller)
200b second control unit (second controller)
200c third control unit
200d fourth control unit (irradiation management device)
201 spot position monitor
202 range shifter
203 range shifter insertion mechanism
204 dose measuring unit
205 movable device
206 main controller
207 movable top plate A
208 movable top plate B
209 wheel
210 ion chamber
211 sensor
212 signal processing device
300 terminal controllers (irradiation management device)
300a monitor
300b input device
400 treatment planning device
500 scanning magnet power supply controller

The invention claimed is:

1. An operating method of a charged particle beam irradiation system comprising a synchrotron for irradiating an affected part of a patient and comprising, in one operating cycle of the synchrotron, steps of injection-capturing, accelerating, extraction controlling, and decelerating, the operating method comprising:
providing a high speed steering system between the synchrotron and an irradiation field forming device;
using the high speed steering system for extracting a part of a charged particle beam accumulated in the synchrotron as a checking beam before an extraction start in the extraction controlling step;
diverging the checking beam extracted from the synchrotron into a beam dump in the high speed steering system by controlling excitation of a steering electromagnet disposed in the high speed steering system downstream of the synchrotron;
providing a multi-layer beam monitor in the high speed steering system and before, in a direction of travel of the checking beam, the beam dump;
measuring a dose distribution of the checking beam to be absorbed into the beam dump by passing the checking beam through the multi-layer beam monitor disposed in the high speed steering system; checking an irradiation depth of the charged particle beam with which the affected part of the patient is to be irradiated, before irradiating the patient, using the dose distribution of the checking beam passing through the multi-layer beam monitor; and
saving and managing the dose distribution of the checking beam.

2. An operating method of a charged particle beam irradiation system comprising a synchrotron for irradiating an affected part of a patient and configured for performing steps of accelerating and decelerating a charged particle beam into different energies multiple times in one operating cycle, and for performing a step of extraction control multiple times during the one operation cycle, the operating method comprising:
providing a high speed steering system between the synchrotron and an irradiation field forming device;
using the high speed steering system and extracting a part of the charged particle beam accumulated in the synchrotron as a checking beam before an extraction start in each extraction control step;
diverging the checking beam extracted from the synchrotron into a beam dump in the high speed steering system by controlling excitation of a steering electromagnet provided in the high speed steering system downstream of the synchrotron;
providing a multi-layer beam monitor in the high speed steering system and before, in a direction of travel of the checking beam, the beam dump;
measuring a dose distribution of the checking beam to be absorbed into the beam dump by passing the checking beam through the multi-layer beam monitor provided in the high speed steering system; checking an irradiation depth of the charged particle beam with which the affected part of the patient is to be irradiated, before irradiating the patient, using the dose distribution of the checking beam passing through the multi-layer beam monitor; and
saving and managing the dose distribution of the checking beam.

3. A charged particle beam irradiation system comprising:
a charged particle beam generator configured to accelerate and extract a charged particle beam;
a first beam transport line connected to the charged particle beam generator and configured to transport the charged particle beam extracted from the charged particle beam generator; and
at least one irradiation device configured to receive the charged particle beam from the charged particle beam generator and to perform irradiation of an affected part of a patient with the charged particle beam,
the charged particle beam irradiation system comprising:
a high speed steering system including a steering electromagnet disposed in the first beam transport line, and a beam dump disposed in a beam pathway diverged from the steering electromagnet, the charged particle beam, which is not transported to the at least one irradiation device among the charged particle beams extracted from the charged particle beam generator, by controlling excitation of the steering electromagnet, being directed to the beam dump in the high speed steering system as a checking beam;
a multi-layer beam monitor disposed in the high speed steering system and configured to measure a dose distribution of the checking beam to be absorbed into the beam dump, the multi-layer beam monitor being disposed in the high speed steering system before, in a direction of travel of the checking beam not transported to the at least one irradiation device, the beam dump, the multi-layer beam monitor providing irradiation information in a depth direction to control the irradiation depth of the charged particle beam with which the affected part of the patient is irradiated in a depth direction of the affected part before irradiation; and
an irradiation management device configured to save and manage the dose distribution of the checking beam measured by the multi-layer beam monitor.

4. The charged particle beam irradiation system according to claim 3, further comprising a dose monitoring device disposed upstream of the multi-layer beam monitor inside the high speed steering system beam dump device and configured to measure a dose of the charged particle beam,
wherein the irradiation management device saves and manages a dose value of the checking beam measured by the dose monitoring device.

5. The charged particle beam irradiation system according to claim 3, further comprising:
a first controller configured to control an extraction start and an extraction stop of the charged particle beam from the synchrotron;
a second controller configured to extract the part of the charged particle beam accumulated in the synchrotron as the checking beam before the extraction start in an extraction control interval in an operating cycle of the synchrotron, and at the same time, to control excitation of the steering electromagnet, to diverge the checking beam extracted from the synchrotron into the high speed steering system.

6. The charged particle beam irradiation system according to claim 4, further comprising:
a first controller configured to control an extraction start and an extraction stop of the charged particle beam from the synchrotron; and
a second controller configured to extract the part of the charged particle beam accumulated in the synchrotron as the checking beam before the extraction start in an extraction control interval in an operating cycle of the synchrotron, and at the same time, to diverge the checking beam extracted from the synchrotron into the high speed steering system by controlling the excitation of the steering electromagnet.

* * * * *